US011275903B1

(12) United States Patent
McInnis

(10) Patent No.: US 11,275,903 B1
(45) Date of Patent: Mar. 15, 2022

(54) SYSTEM AND METHOD FOR TEXT-BASED CONVERSATION WITH A USER, USING MACHINE LEARNING

(71) Applicant: Retain Health, Inc, Bedford, MA (US)

(72) Inventor: Mark McInnis, Bedford, MA (US)

(73) Assignee: Retain Health, Inc, Bedford, MA (US)

( * ) Notice: Subject to any disclaimer, the term of this patent is extended or adjusted under 35 U.S.C. 154(b) by 0 days.

(21) Appl. No.: 17/319,138

(22) Filed: May 13, 2021

(51) Int. Cl.
| | |
|---|---|
| *G16H 50/20* | (2018.01) |
| *G06F 40/35* | (2020.01) |
| *G06N 20/00* | (2019.01) |
| *G06F 40/284* | (2020.01) |
| *G06N 5/04* | (2006.01) |
| *G06F 40/205* | (2020.01) |

(52) U.S. Cl.
CPC ............ *G06F 40/35* (2020.01); *G06F 40/284* (2020.01); *G06N 5/04* (2013.01); *G06N 20/00* (2019.01); *G16H 50/20* (2018.01); *G06F 40/205* (2020.01)

(58) Field of Classification Search
CPC ................................ G16H 50/20; G06N 20/00
See application file for complete search history.

(56) References Cited

U.S. PATENT DOCUMENTS

| | | | | |
|---|---|---|---|---|
| 9,424,532 | B1 * | 8/2016 | Abedini | ................. G16H 50/20 |
| 10,847,261 | B1 | 11/2020 | Neumann | |
| 10,918,910 | B2 * | 2/2021 | Lutz | .................... A63B 24/0087 |
| 2003/0040002 | A1 | 2/2003 | Ledley | |
| 2005/0273317 | A1 * | 12/2005 | Brill | ....................... G06F 40/253 704/9 |
| 2007/0203761 | A1 * | 8/2007 | Keen | ...................... G16H 50/70 705/5 |
| 2009/0287070 | A1 * | 11/2009 | Baker, Jr. | ............... G16H 50/20 600/324 |
| 2009/0307179 | A1 | 12/2009 | Colby | |
| 2014/0074454 | A1 * | 3/2014 | Brown | ................... G06F 3/167 704/9 |
| 2015/0379232 | A1 * | 12/2015 | Mainwaring | .......... G16H 10/20 705/2 |
| 2016/0291036 | A1 | 10/2016 | O'Bryant | |
| 2016/0364537 | A1 * | 12/2016 | Das | ........................ G16H 50/70 |
| 2017/0098051 | A1 * | 4/2017 | Balram | .................. G16H 70/20 |
| 2017/0286622 | A1 * | 10/2017 | Cox | ....................... G06N 5/025 |

(Continued)

OTHER PUBLICATIONS https://link.springer.com/content/pdf/10.14283/jpad.2020.45.pdf Title: The Trial-Ready Cohort for Preclinical/Prodromal Alzheimer's Disease Date: Aug. 11, 2020 By: AISEN.

*Primary Examiner* — Jialong He
(74) *Attorney, Agent, or Firm* — Caldwell Intellectual Property Law; Katherine Rubino

(57) ABSTRACT

In an aspect, systems and methods for text-based conversation with a user, using machine learning, include receiving, using a computing device, at least a feature associated with the user's condition and at least a preference input; generating, using the computing device, a probabilistic output by operating a probabilistic machine learning model input with the at least a feature; classifying, using the computing device, an intervention class by operating a classifying machine learning model input with the probabilistic output and the at least a feature; and, interfacing conversationally, using the computing device, with the user by text generated as a function of the intervention class and the at least a preference input.

18 Claims, 9 Drawing Sheets

(56) References Cited

U.S. PATENT DOCUMENTS

| | | | | |
|---|---|---|---|---|
| 2018/0137941 A1* | 5/2018 | Chen | .................. | G16H 50/50 |
| 2018/0166174 A1 | 6/2018 | Lewis | | |
| 2018/0342323 A1* | 11/2018 | Shankar | ................ | G06N 7/005 |
| 2019/0200915 A1 | 7/2019 | Baker | | |
| 2019/0216392 A1 | 7/2019 | Bower | | |
| 2020/0097814 A1* | 3/2020 | Devesa | ................ | G06N 3/006 |
| 2020/0185100 A1 | 6/2020 | Francois | | |
| 2020/0411170 A1* | 12/2020 | Brown | ........... | G06Q 10/063114 |
| 2021/0134425 A1* | 5/2021 | Mason | .................. | A61B 34/25 |

* cited by examiner

SYSTEM AND METHOD FOR TEXT-BASED CONVERSATION WITH A USER, USING MACHINE LEARNING

FIELD OF THE INVENTION

The present invention generally relates to the field of artificial intelligence, simulation, and modeling. In particular, the present invention is directed to text-based conversation with a user, using machine learning.

BACKGROUND

Machine generated text-based conversation is commonly employed for a number of applications, including commerce, education, entertainment, finance, health, news, and productivity. Commonly, machine generated text-based conversation responds with general pre-prepared responses to all users in all contexts. As a result, machine generated test-based conversation is unable to respond to users in a way meaningful to specifically to them.

SUMMARY OF THE DISCLOSURE

In an aspect, a method of text-based conversation with a user, using machine learning, includes receiving, using a computing device, at least a feature associated with the user's condition and at least a preference input; generating, using the computing device, a probabilistic output, where generating the probabilistic output additionally includes inputting the at least a feature to a probabilistic machine learning model and generating the probabilistic output as a function of the probabilistic machine learning model; classifying, using the computing device, the probabilistic output and the at least a feature to an intervention class, where classifying additionally includes inputting the probabilistic output and the at least a feature to a classifying machine learning model and classifying the probabilistic output and the at least a feature to the intervention class as a function of the classifying machine learning model; and interfacing conversationally, using the computing device, with the user, where interfacing conversationally additionally includes generating text as a function of the intervention class and the at least a preference input and interfacing conversationally using the generated text.

In another aspect a system for text-based conversation with a user, using machine learning, includes a computing device configured to receive at least a feature associated with the user's condition and at least a preference input; generate a probabilistic output, where generating the probabilistic output additionally includes inputting the at least a feature to a probabilistic machine learning model and generating the probabilistic output as a function of the probabilistic machine learning model; classify the probabilistic output and the at least a feature to an intervention class, where classifying additionally includes inputting the probabilistic output and the at least a feature to a classifying machine learning model and classifying the probabilistic output and the at least a feature to the intervention class as function of the classifying machine learning model; and, interface conversationally with the user, where interfacing conversationally additionally includes generating text as a function of the intervention class and the at least a preference input and interfacing conversationally using the generated text.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for text-based conversation with a user, using machine learning. In an embodiment, machine-learning may be used to determine a probabilistic output from user inputs, such as without limitation a feature and/or a preference input. In some cases, text may be generated as a function of one or more of a probabilistic output and a preference input. Text may then be used to interface conversationally with user, in a purposeful and user-specific manner.

Aspects of the present disclosure can also be used to assess a user according to a probabilistic output as a function of one or more inputs from the user. Aspects of the present disclosure can be used to recommend and monitor an intervention as a function of input from a user. This is so, at least in part, because the present disclosure provides a text-based interface with user, which is a function of one or more features or preferences input by the user.

Aspects of the present disclosure allow for text-based conversation with a user, using machine learning. Exemplary embodiments illustrating aspects of the present disclosure are described below in the context of several specific examples.

Figure 1:
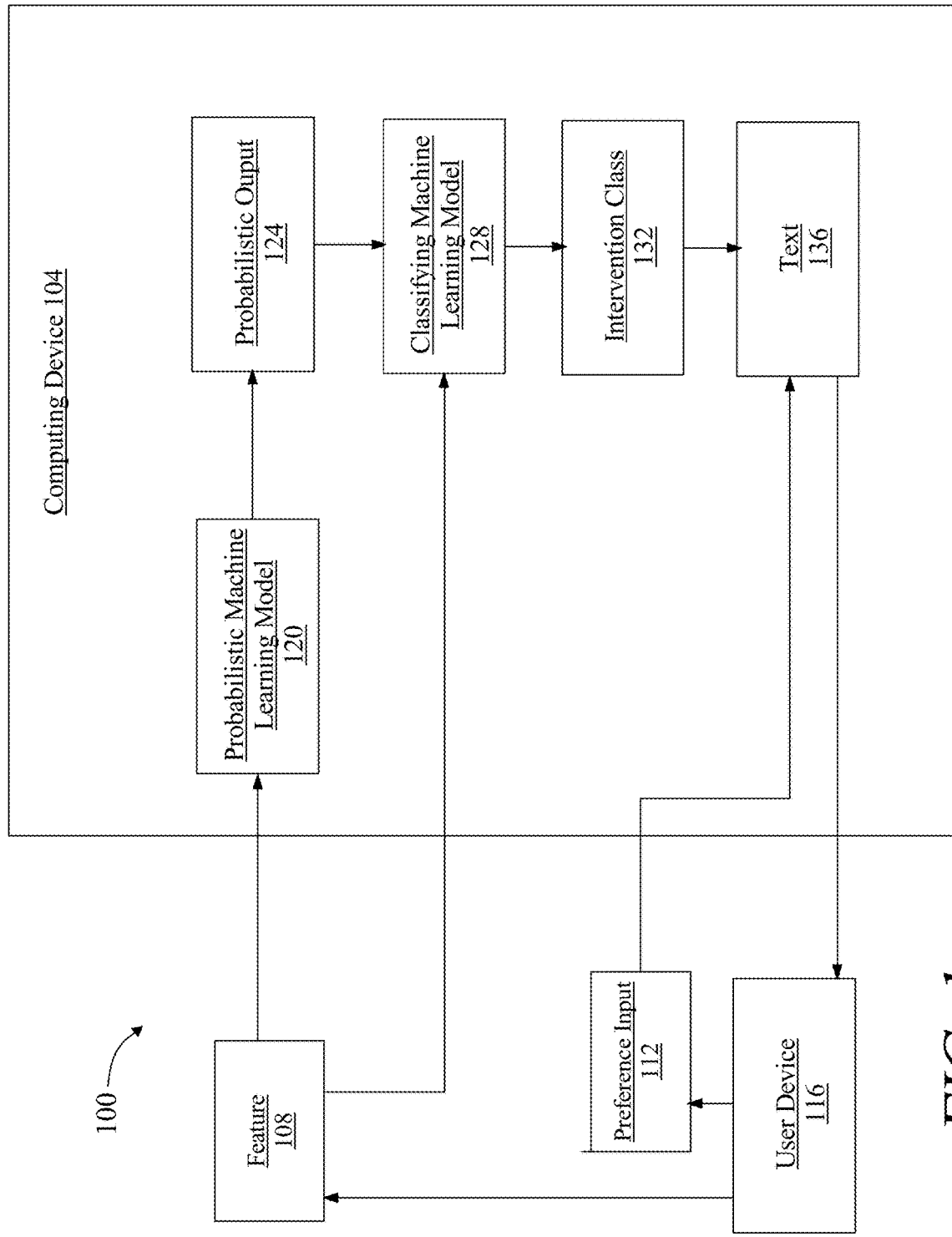
FIG. 1 is a block diagram of an exemplary embodiment of a system for text-based conversation with a user, using machine learning.

Referring now to FIG. 1, an exemplary embodiment of a system 100 for text-based communication with a user, using machine learning is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 receives at least a feature 108 and at least a preference input 112 from a user. In some embodiments, at least a feature 108 may include one or more of a continuous value, a discrete value, an answer to an interview question, or a Boolean (e.g., True/False) value. In some embodiments, preference input 112 may include, without limitation, one or more of a prioritization ranking, a preferred selection, or a discrete value. In some embodiments, user may be communicating directly with a computing device 104. Alternatively or additionally, in some cases, user may be communication by way of a user device 116. An exemplary list of user devices may include a personal computer, fax, telephone, or smart phone. In some embodiments, communication between computing device 104 and user device 116 is performed by way of text-based messages, such as without limitation short message service (SMS) messages. Communication with user device 116 and computing device 104 may, in some cases, also be performed by way of one or more networks, such as without limitation the Internet.

Continuing with reference to FIG. 1, computing device 104 inputs at least a feature 108 to a probabilistic machine learning model 120 and generates a probabilistic output 124 using the probabilistic machine learning model 120. In some embodiments, probabilistic machine learning model 120 may be accessed, for example from any of a storage component, a database, or another computing device. In some cases, probabilistic machine learning model 120 may be accessed from another computing device by way of one or more networks, such as without limitation the Internet. In some embodiments, computing device 104 may be additionally configured to train a probabilistic machine learning model 120. Probabilistic machine-learning model may include any machine-learning model as described in this disclosure. Computing device 104 may train probabilistic machine learning model 120 using training data. Training data may include a plurality of training examples. Each training example of plurality of training examples may correlate one or more features to or with one or more probabilistic outcomes and/or other elements of data usable for computation of probabilistic outcomes. Computing device 104 may train probabilistic machine learning model 120 as a function of and/or using any machine learning algorithm as described in this disclosure. In some cases, and as a non-limiting example, probabilistic machine learning algorithm may include one or more of a supervised machine learning algorithm and an unsupervised machine learning algorithm. In some cases, and without limitation, plurality of features may include one or more of inputs or outputs used for training a machine learning algorithm. Training data may include any training data described in this disclosure. Training data and/or training examples may include at least a feature related to a user's condition. At least a feature related to a user's condition may, in some cases, be received from one or more evidential resources, such as without limitation refereed journal articles demonstrating a significant correlation between the at least a feature and the condition.

Alternatively or additionally, in some embodiments, at least a feature related to a user's condition may be received from experiential resources, such as without limitation correlations derived through a medical practice involving treatment of the condition. Alternatively or additionally, in some embodiments, at least a feature related to a user's condition may be include assessment results of assessments used for determining a severity of a condition, such as without limitation a brief cognitive assessment. In some embodiments, probabilistic machine learning model 120 may be trained using an unsupervised machine learning algorithm and training data; and the training data includes a plurality of features. "Training data," as used herein in this disclosure, is data containing correlations that a machine-learning process may use to model relationships between two or more categories of data elements. For instance, and without limitation, training data may include a plurality of features, each feature representing a set of data elements that were recorded, received, and/or generated together; data elements may be correlated by shared existence in a given data entry, by proximity in a given data entry, or the like. Multiple data entries in training data may evidence one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As an example, a feature selected from an evidential resource may be included as training data, where results presence of features significantly correlated with a health condition are provided as input elements, which are correlated to higher or lower probabilistic outputs. As another example, results from a mini-cog cognitive assessment may be included as training data, where results indicative of poor performance on the assessment are provided as input elements, which are correlated to higher or lower probabilistic outputs. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure. As a non-limiting illustrative example, input data includes features 108 and probabilistic outputs 124 and output data includes intervention classes 132, such that the features and probabilistic outputs are correlated by a machine-learning model to corresponding intervention classes 132.

Still referring to FIG. 1, computing device 104 operates a classifying machine learning model 128 input with probabilistic output 124 and at least a feature 108 to classify an intervention class 132. In some embodiments, classifying machine learning model 120 is trained using any of a number of machine learning algorithms described in this disclosure, such as without limitation a supervised machine learning algorithm or an unsupervised machine learning algorithm. In some embodiments, classifying machine learning model 128 is trained using any of a number of optimization algorithms described in this disclosure, such as without limitation a linear optimization algorithm. In some embodiments, intervention class 132 may include, without limitation, a class of lifestyle change for user. In some embodiments, classifying machine learning model 128 may be trained using a supervised machine learning algorithm and training data; and the training data includes a plurality of features. In some cases, plurality of features may include one or more of inputs or outputs used for training a supervised machine learning algorithm. Training data may include any training data described in this disclosure. In some embodiments, classifying machine learning model 128 may be trained using an unsupervised machine learning algorithm and training data; and the training data includes a plurality of features. In some cases, plurality of features may include one or more of inputs or outputs used for training an unsupervised machine learning algorithm. Training data may include any training data described in this disclosure. In some embodiments, computing device 104 may additionally configured to select classifying machine learning model 128 from a plurality of classifying machine learning models, as a function of at least a feature 108; where, the classifying machine learning model 128 was trained using training data comprising a plurality of inputs. In some cases, selected classifying machine learning model 128 may be chosen based upon at least a feature 108 directly. Alternatively or additionally, in some cases, selected classifying machine learning model 128 may be chosen based upon one or more calculations made using at least a feature 108. In some cases, plurality of features may include one or more of inputs or outputs used for training a machine learning algorithm.

Training data may include any training data described in this disclosure. In some embodiments, computing device 104 may additionally be configured to select training data from a plurality of training data, as a function of at least one feature 108; and train classifying machine learning model 128 using the training data. In some cases, selected training may be chosen based upon at least a feature 108 directly. Alternatively or additionally, in some cases, selected training data may be chosen based upon one or more calculations made using at least a feature 108. In some cases, plurality of features may include one or more of inputs or outputs used for training a machine learning algorithm. Training data may include any training data described in this disclosure. In some embodiments, classifying machine learning model 128 may be accessed, for example from any of a storage component, a database, or another computing device. In some cases, classifying machine learning model 128 may be accessed from another computing device by way of one or more networks, such as without limitation the Internet. In some embodiments, computing device 104 is additionally configured to train classifying machine learning model 128, wherein training the classifying machine learning model 128 further comprises inputting training data to a machine learning algorithm, wherein the training data comprises a plurality of features; and training the classifying machine learning model 128 as a function of the machine learning algorithm. Training data may include any training data described in this disclosure, such as for example at least a feature related to a user's condition. At least a feature related to a user's condition may, in some cases, be selected from an evidential resources, such as without limitation refereed journal articles demonstrating a significant correlation between the at least a feature and an intervention class used to treat the condition. Alternatively or additionally, in some embodiments, at least a feature related to a user's condition may be selected from an experiential resources, such as without limitation correlations derived through a medical practice involving treatment of the condition. Alternatively or additionally, in some embodiments, at least a feature related to a user's condition may be include assessment results of assessments used for determining a severity of a condition and/or an intervention class useful in treating the condition.

Still referring to FIG. 1, In some embodiments, classifying machine learning model 128 may include a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(AB)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, in some embodiments, computing device 104 may classify an intervention class 132 by using one or more optimization algorithms. For example, in some cases, an intervention class 132 is classified from a finite plurality of intervention classes, by way of an optimization algorithm.

Still referring to FIG. 1, computing device 104 may compute a score associated with each of a plurality of intervention classes and select an intervention class to minimize and/or maximize the score, depending on whether an optimal result is represented, respectively, by a minimal and/or maximal score; a mathematical function, described herein as an "objective function," may be used by computing device 104 to score each possible pairing. Objective function may be based on one or more objectives as described below. Computing device 104 may classify an intervention class 132 with a user, that optimizes objective function, such that without limitation the user's condition is maximally benefitted. In some embodiments, exemplary intervention classes 132 may include, without limitation interventions related to one of the user's diet, exercise, sleep, cognitive activity, and social engagement. In various embodiments a score of a particular intervention class 132 may be based on a combination of one or more factors, including without limitation a probabilistic output 124 and at least a feature 108. Each factor may be assigned a score based on predetermined variables. In some embodiments, the assigned scores may be weighted or unweighted.

Still referring to FIG. 1, optimization of objective function may include performing a greedy algorithm process. A "greedy algorithm" is defined as an algorithm that selects locally optimal choices, which may or may not generate a globally optimal solution. For instance, computing device 104 may select an intervention class 132 so that scores associated therewith are the best score for each feature 108. In such an example, optimization may determine the combination of intervention class 132 that best addresses a user's condition, such that an intervention belonging to the intervention class 132, when implemented will introduce greatest benefit to a user's condition.

Still referring to FIG. 1, objective function may be formulated as a linear objective function, which computing device 104 may solve using a linear program such as without limitation a mixed-integer program. A "linear program," as used in this disclosure, is a program that optimizes a linear objective function, given at least a constraint. For instance, in some embodiments, an intervention class 132 may be classified to minimize a user's risk score for a condition; the user's risk score may be represented as a probabilistic output 124; and the intervention class 132 is classified to minimize the user's risk score when an intervention for the classified intervention class 132 is implemented. In various embodiments, system 100 may determine an intervention class that maximizes a total score subject to a constraint that precludes implementation of certain candidate intervention classes. A mathematical solver may be implemented to solve for an intervention class 132 that maximizes scores; mathematical solver may be implemented on computing device 104 and/or another device in system 100, and/or may be implemented on third-party solver.

With continued reference to FIG. 1, optimizing objective function may include minimizing a loss function, where a "loss function" is an expression of an output, which an optimization algorithm minimizes to generate an optimal result. As a non-limiting example, computing device 104 may assign variables relating to a set of parameters, which may correspond to score components as described above, calculate an output of mathematical expression using the variables, and select an intervention class 132 that produces an output having the lowest size, according to a given definition of "size," of the set of outputs representing each of plurality of candidate ingredient combinations; size may, for instance, included absolute value, numerical size, or the like. Selection of different loss functions may result in identification of different potential pairings as generating minimal outputs.

Still referring to FIG. 1, computing device 104 interfaces conversationally with user, for example without limitation by way of user device 116, using text 136 generated as a function of intervention class 132 and a preference input 112. In some embodiments, computing device 104 selects a particular intervention belonging to an intervention class 132, using a preference input from user; and the particular intervention is a subject of text 136 communicated to the user. In some cases, computing device 104 may generate text 136 by accessing pre-prepared text, which is stored by the computing device 104, such as without limitation within a database. According to some embodiments, computing device 104 may interface conversationally with user by using a chatbot, as described in this application. In some embodiments, computing device 104 may be configured to interface conversationally by performing natural language processing. Natural language processing may include any methods and/or processes for natural language processing described in this disclosure. Alternatively or additionally, in some embodiments, computing device 104 may interface conversationally with user by using a language processing module. Language processing module may include any hardware and/or software module. Language processing module may be configured to extract, from the one or more documents, one or more words. One or more words may include, without limitation, strings of one or more characters, including without limitation any, sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module may operate to produce a language processing model. Language processing model may include a program automatically generated by computing device and/or language processing module to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like.

Still referring to 1, language processing module and/or diagnostic engine may generate the language processing model by any suitable method, including without limitation a natural language processing classification algorithm; language processing model may include a natural language process classification model that enumerates and/or derives statistical relationships between input terms and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (H M M). HMMs as used herein are statistical models with inference algorithms that that may be applied to the models. In such models, a hidden state to be estimated may include an association between an extracted words, phrases, and/or other semantic units. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module may use a corpus of documents to generate associations between language elements in a language processing module, and diagnostic engine may then use such associations to analyze words extracted from one or more documents and determine that the one or more documents indicate significance of a category. In an embodiment, language module and/or [computing device] may perform this analysis using a selected set of significant documents, such as documents identified by one or more experts as representing good information; experts may identify or enter such documents via graphical user interface, or may communicate identities of significant documents according to any other suitable method of electronic communication, or by providing such identity to other persons who may enter such identifications into [computing device]. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine may automatically obtain the document using such an identifier, for instance by submitting a request to a database or compendium of documents such as JSTOR as provided by Ithaka Harbors, Inc. of New York.

Still referring to FIG. 1, in some embodiments, computing device 104 may additionally be configured to interface conversationally with a user, for example by way of a user device, wherein interfacing conversationally additionally includes: receiving a submission; recognizing at least a word from the submission, wherein recognizing the at least a word further comprises: inputting the submission to a language processing model; and, recognizing the at least a word as a function of the language processing model; and generating a response as a function of the at least a word. In some cases, computing device may be further configured to: train language processing model, wherein training the language processing model further comprises inputting training data to a natural language processing algorithm; and training the language processing model as a function of the natural language processing algorithm.

Still referring to FIG. 1, in some embodiments, computing device 104 may additionally be configured to reperform one or more functions after having interfaced conversationally with a user. For instance, computing device 104 may be configured to iteratively reperform one or more functions, including those described immediately below, any number of times. In some embodiments, computing device 104 may additionally be configured to wait for a timeframe to elapse, receive at least a second feature 108 associated with a user's condition and at least a second preference input 112, generate a second probabilistic output 124, and classify a second intervention class 132. In some cases. generating a second probabilistic output 124 may additionally include inputting at least a second feature 108 to a probabilistic machine learning model 120 and generating the second probabilistic output 124 as a function of the probabilistic machine learning model 120. In some cases, classifying a second intervention class may additionally include inputting a second probabilistic output 124 and an at least a second preference input 112 to a classifying machine learning model 128 and classifying the second probabilistic output 124 and the at least a second preference input 112 to the second intervention class 132. In some cases, a timeframe, which computing device may be configured to wait, may be predetermined; for example, the timeframe may be within a range of between about 1 to 10 weeks, a range of between about 3 to 8 weeks, or a range of between about 6 to 8 weeks. Alternatively or additionally, in some cases, a timeframe may be determined during the timeframe; for example, in some cases, the timeframe may be determined as a function of user submissions, which are received while user device 104 is interfacing conversationally with user.

Still referring to FIG. 1, in some embodiments, computing device 104 may be further configured to generate at least a metric, wherein generating the at least a metric further comprises: inputting the intervention class to a machine learning model; and generating the at least a metric as a function of the machine learning model. In some cases, computing device 104 may be further configured to receive a submission from the user; recognize at least a datum from the submission, wherein recognizing the at least a datum further comprises: inputting the submission to a language processing model; and, recognizing the at least a datum as a function of the language processing model; wherein the at least a datum is associated with the at least a metric. In some cases, at least a metric may be associated with an intervention class 132; and the at least a metric may be a useful measure of progress made through implementing an intervention belonging to the intervention class 132. Likewise, in some cases, at least a datum may be associated with at least a metric; and the at least a datum may be an actual measure of progress made through implementing an intervention belonging to the intervention class 132.

Figure 2:
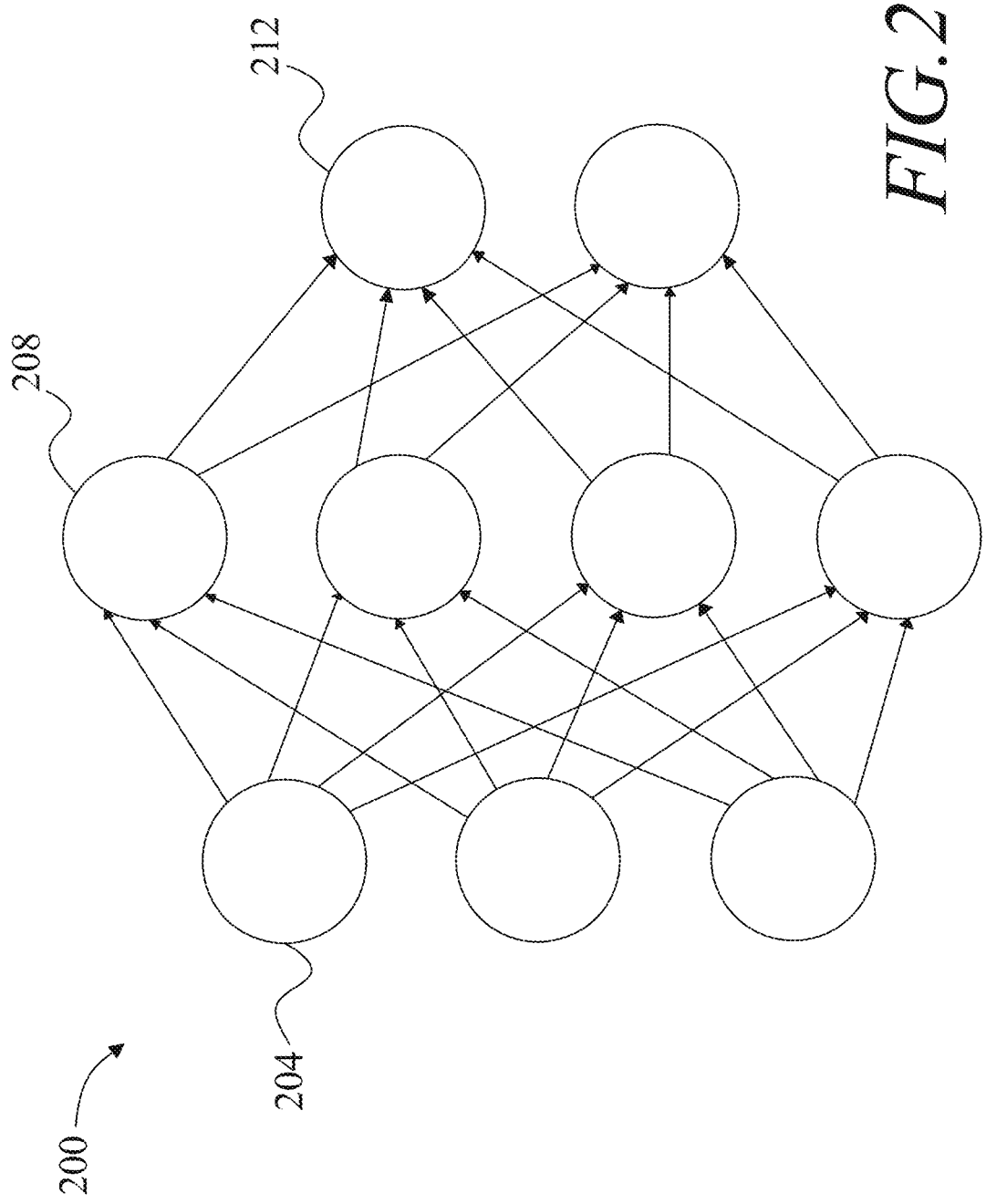
FIG. 2 is a schematic diagram of an exemplary embodiment of a neural network.

Referring now to FIG. 2 an exemplary embodiment of neural network 200 is illustrated. Neural network also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 204, one or more intermediate layers 208, and an output layer of nodes 212. Connections between nodes may be created via the process of "training" the network, in which elements from a training dataset are applied to input nodes 204, a suitable training algorithm (such as Levenberg-Marquardt, conjugate gradient, simulated annealing, or other algorithms) is then used to adjust the connections and weights between nodes in adjacent layers 208 of the neural network to produce the desired values at output nodes 212. This process is sometimes referred to as deep learning.

Figure 3:
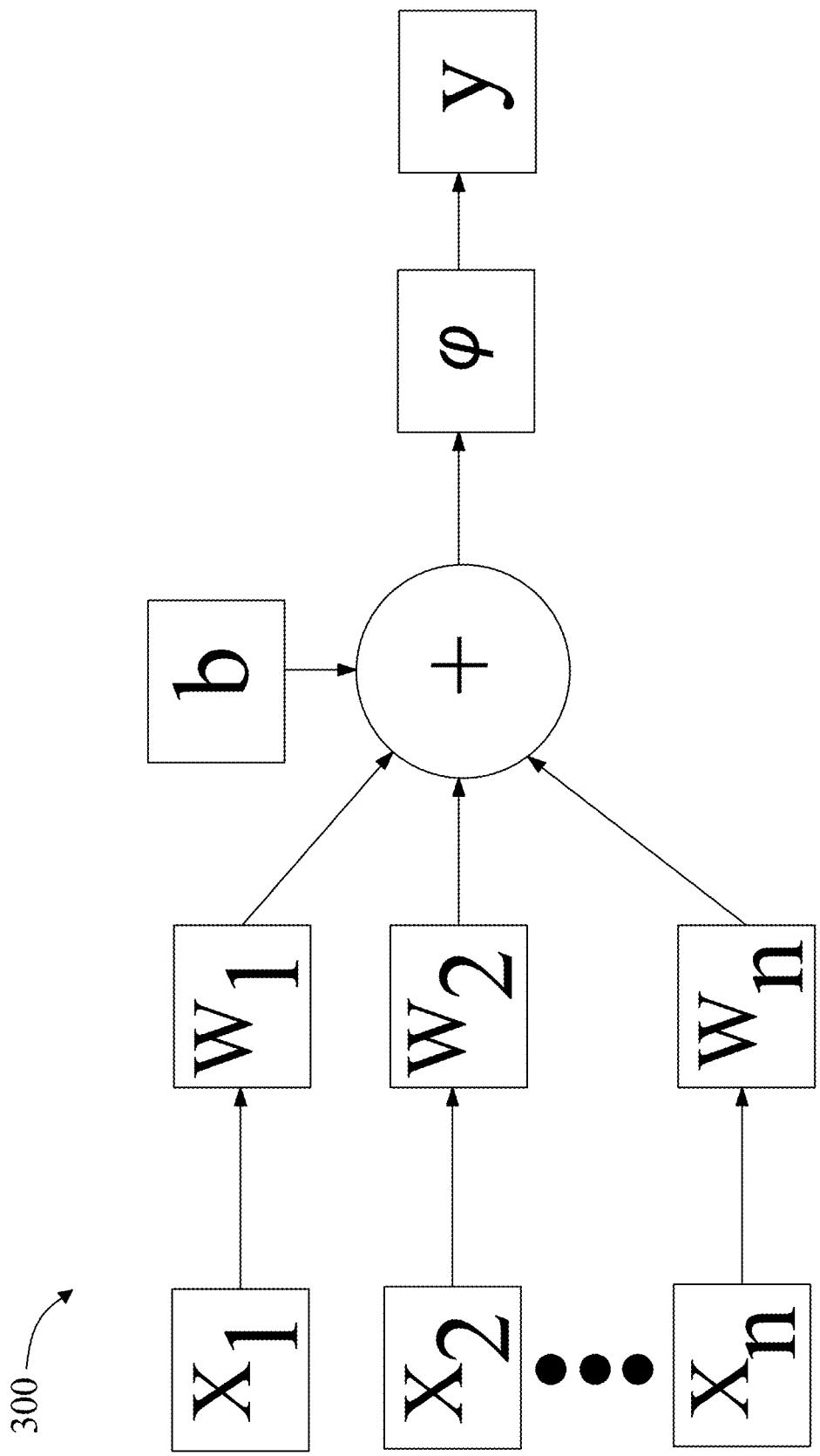
FIG. 3 is a schematic diagram of an exemplary embodiment of a node of a neural network.

Referring now to FIG. 3, an exemplary embodiment of a node 300 of a neural network is illustrated. A node 300 may include, without limitation a plurality of inputs $x_i$ that may receive numerical values from inputs to a neural network containing the node and/or from other nodes. Node 300 may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Still referring to FIG. 3, a neural network may, for example without limitation, receive at least a feature 108 and/or at least a probabilistic output 128 as inputs and output an intervention class 132 and a classification score representing a probability of classification to a predetermined class according to weights $w_i$ that are derived using machine-learning processes as described in this disclosure.

Referring again to FIG. 1, computing device 104, in some embodiments may be configured to interface conversationally with a user by way of a chatbot. Chatbot, in some cases, may be used to generate text 136 that is used to interface conversationally with user. In some versions, user may respond to computing device 136, by way of a text-based interface, for example without limitation short message service (SMS) text message.

Figure 4:
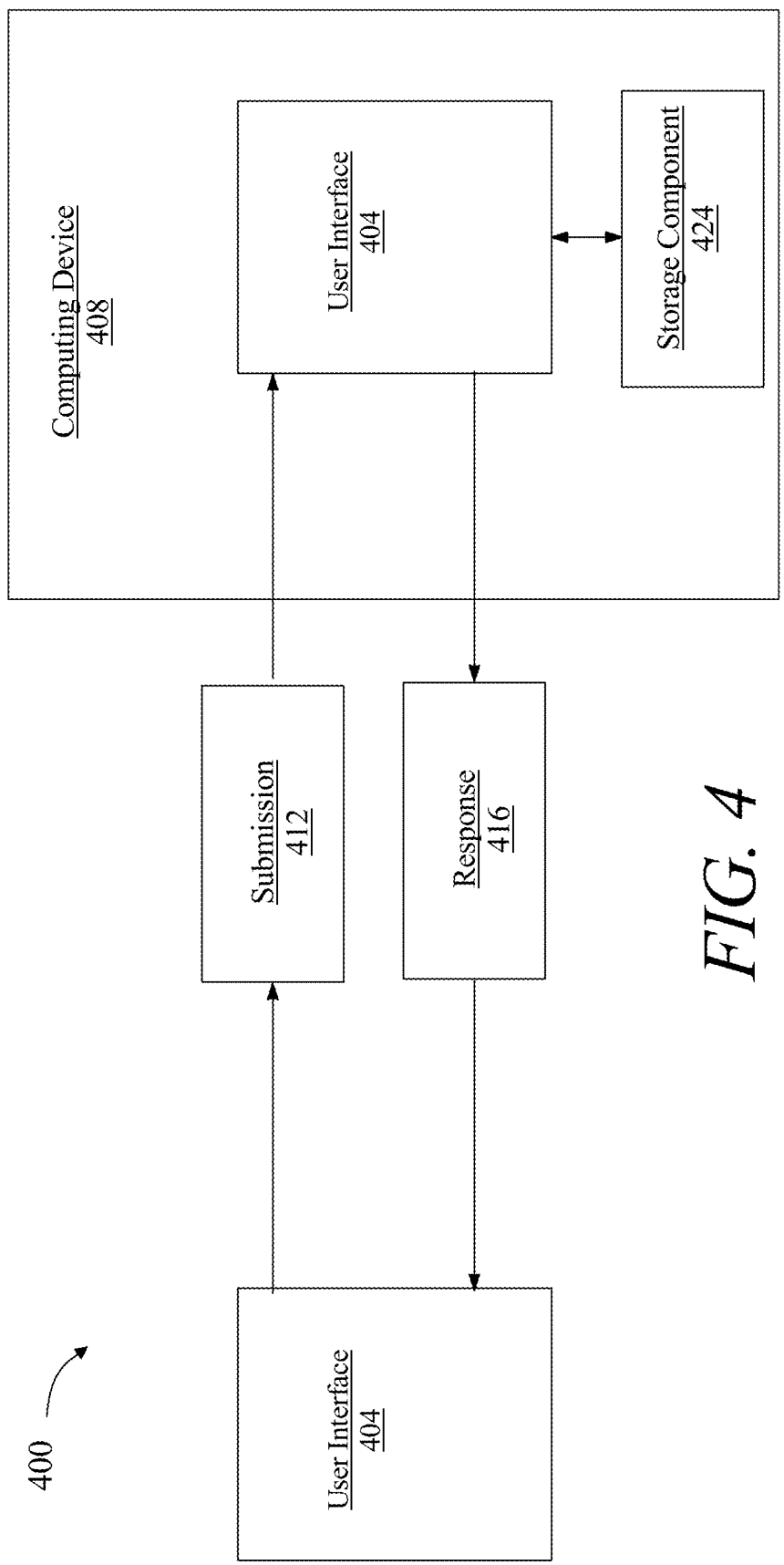
FIG. 4 is a schematic diagram of an exemplary embodiment of a chatbot.

Referring to FIG. 4, a chatbot system 400 is schematically illustrated. According to some embodiments, a user interface 404 may be communicative with a computing device 408 that is configured to operate a chatbot. In some cases, user interface 404 may be local to computing device 408. Alternatively or additionally, in some cases, user interface 404 may remote to computing device 408 and communicative with the computing device 408, by way of one or more networks, such as without limitation the internet. Alternatively, or additionally, user interface 404 may communicate with user device 408 using telephonic devices and networks, such as without limitation fax machines, short message service (SMS), or multimedia message service (MMS). Commonly, user interface 404 communicates with computing device 408 using text-based communication, for example without limitation using a character encoding protocol, such as American Standard for Information Interchange (ASCII). Typically, a user interface 404 conversationally interfaces a chatbot, by way of at least a submission 412, from the user interface 408 to the chatbot, and a response 416, from the chatbot to the user interface 404. In many cases, one or both of submission 412 and response 416 are text-based communication. Alternatively or additionally, in some cases, one or both of submission 412 and response 416 are audio-based communication. According to some embodiments, text-based communication may include at least a network location address, such as without limitation a hyperlink or uniform resource locator (URL), which may direct a user to more information, including without limitation videos, images, infographics, websites, audio, and text.

Continuing in reference to FIG. 4, a submission 412 once received by computing device 408 operating a chatbot, may be processed by a processor 420. In some embodiments, processor 420 processes a submission 4112 using one or more of keyword recognition, pattern matching, and natural language processing. In some embodiments, processor employs real-time learning with evolutionary algorithms. In some cases, processor 420 may retrieve a pre-prepared response from at least a storage component 424, based upon submission 412. Alternatively or additionally, in some embodiments, processor 420 communicates a response 416 without first receiving a submission 412, thereby initiating conversation. In some cases, processor 420 communicates an inquiry to user interface 404; and the processor is configured to process an answer to the inquiry in a following submission 412 from the user interface 404. In some cases, an answer to an inquiry present within a submission 412 from a user device 404 may be used by computing device 104 as an input to another function, for example without limitation at least a feature 108 or at least a preference input 112.

Figure 5:
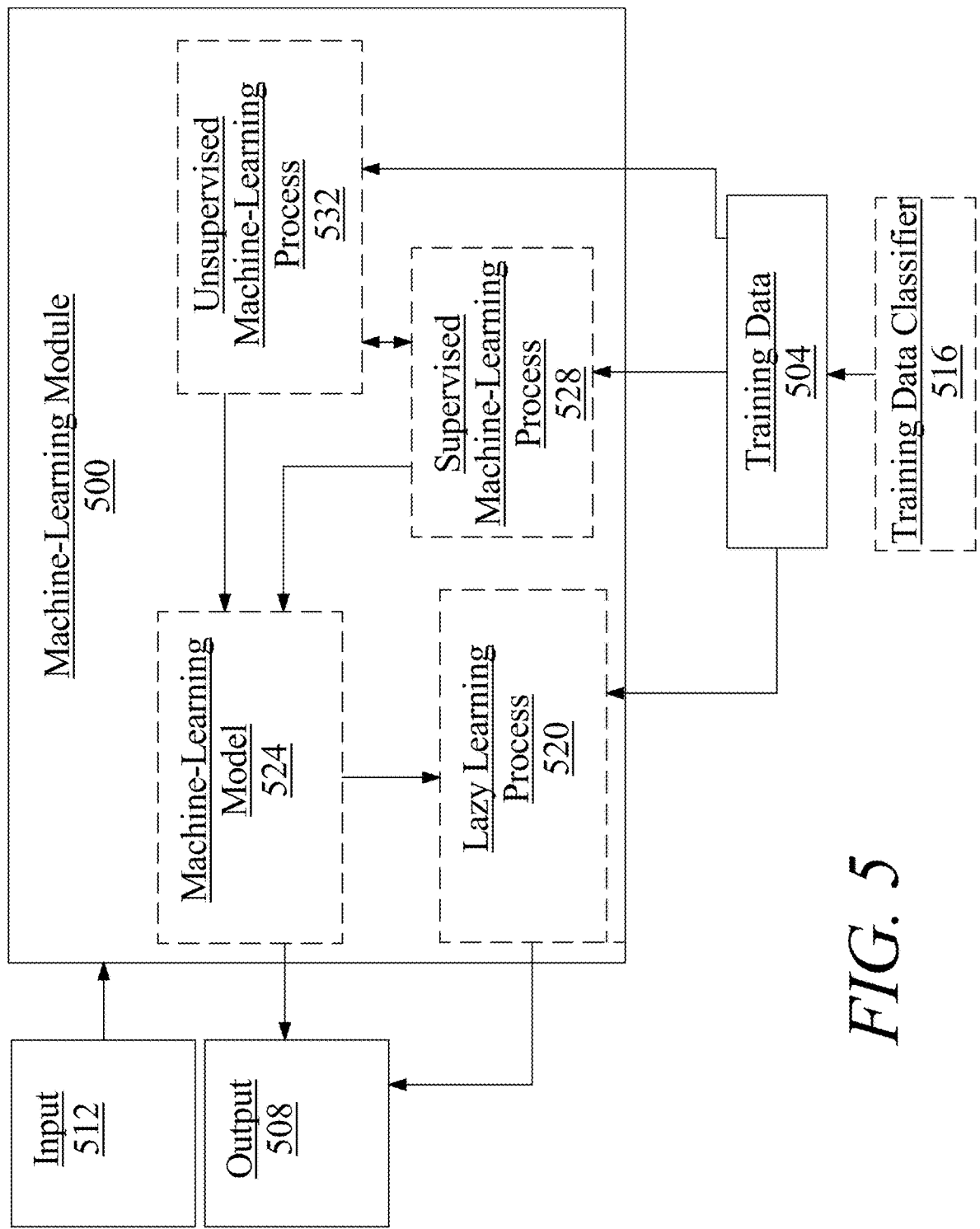
FIG. 5 is a block diagram illustrating an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example inputs may include at least a feature 108, a probabilistic output 124, and/or at least a preference input 112; and outputs may include a probabilistic output 124 and/or an intervention class 132.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data as a function of at least a feature 108. In some cases, at least a feature 108 may be used to filter training data; for example, the at least a feature 108 may be used to preclude certain training datasets.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include at least a feature 108, at least a preference input 112, and/or a probabilistic output 124 as described above as inputs, a probabilistic output 124 and/or a intervention class as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naive Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
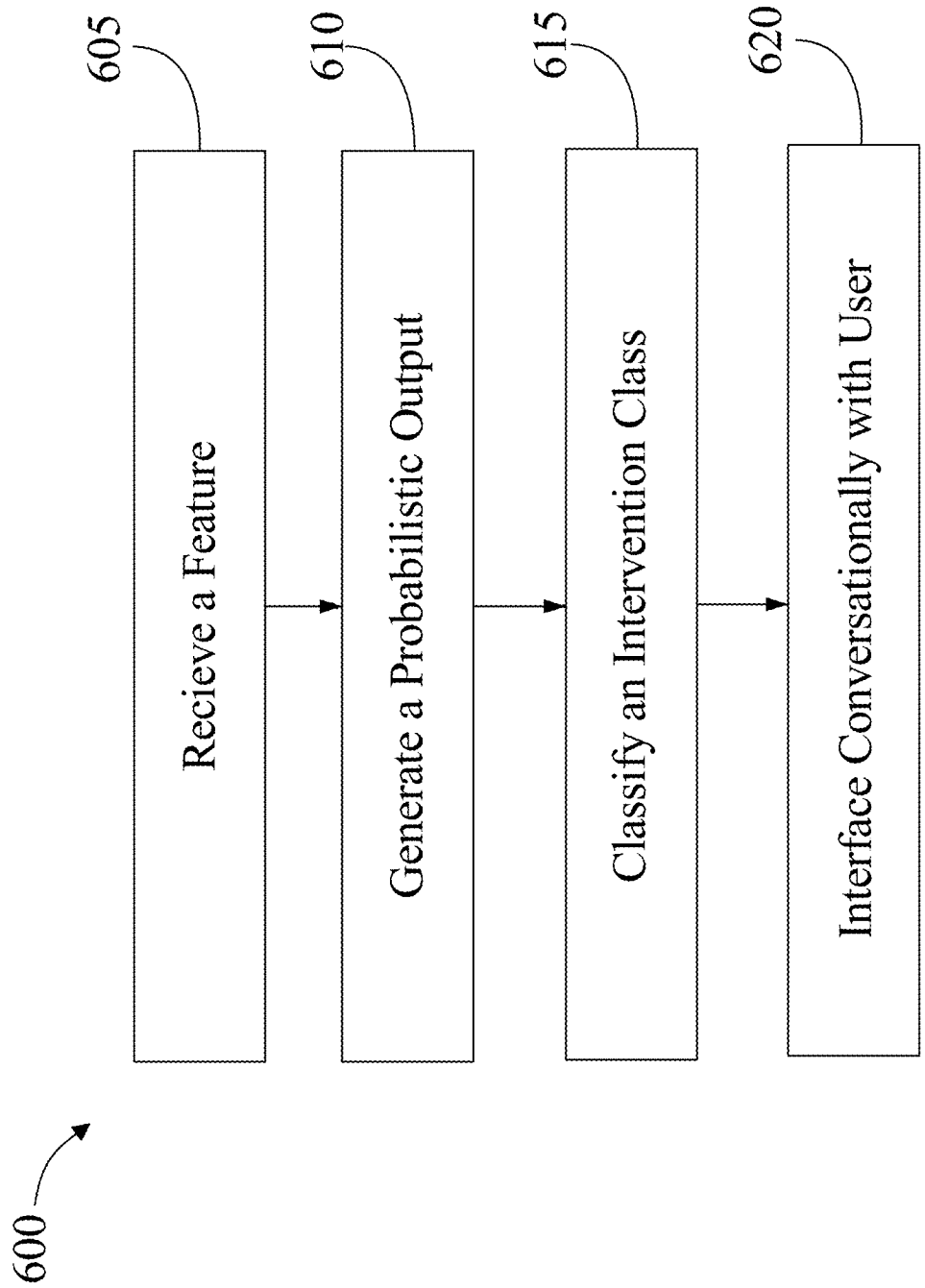
FIG. 6 is a flow diagram illustrating an exemplary embodiment of a method of text-based conversation with a user, using machine learning.

Referring to FIG. 6, a method 600 of text-based conversation with a user, using machine learning is diagrammed by way of a flow chart. At step 605, computing device 104 receives at least a feature 108 associated with a user's condition and at least a preference input 112; this may be implemented, without limitation, in any manner described above in reference to FIGS. 1-5. Computing device 104 may include any computing device 104 as described above in reference to FIGS. 1-5. A feature 108 may include any feature 108 described above in reference to FIGS. 1-5. A preference input 112 may include any preference input 112 described above in reference to FIGS. 1-5.

Still referring to FIG. 6, at step 610, computing device 104 generates a probabilistic output 124, wherein generating a probabilistic output 124 includes inputting at least a feature 104 to a probabilistic machine learning model 120; and generating the probabilistic output 120 as a function of the probabilistic machine learning model 120. Probabilistic output 124 may include any probabilistic outputs described above, in reference to FIGS. 1-5. Probabilistic machine learning model 120 may include any machine learning model 120 described above, in reference to FIGS. 1-5. In some embodiments, probabilistic machine learning model 120 may be trained using a supervised machine learning algorithm and training data, comprising a plurality of features. A supervised machine learning algorithm may include any supervised machine learning algorithm described above, in reference to FIGS. 1-5. Training data may include any training data described above, in reference to FIGS. 1-5. A plurality of features may include any plurality of features described above, in reference to FIGS. 1-5. In some embodiments, probabilistic machine learning model 120 may be trained using an unsupervised machine learning algorithm and training data, comprising a plurality of features. An unsupervised machine learning algorithm may include any unsupervised machine learning algorithm described above, in reference to FIGS. 1-5.

Still referring to FIG. 6, at step 615, computing device 104 classifies an intervention class 132, wherein classifying the intervention class 132 includes: inputting a probabilistic output 124 and at least a feature 108 to a classifying machine learning model 128 input; and classifying the probabilistic output 124 and the at least a feature 108 to the intervention class 132. Intervention class 132 may include any intervention classes 132 described above, in reference to FIGS. 1-5. Classifying machine learning model 128 may include any machine learning model 128 described above, in reference to FIGS. 1-5. In some embodiments, classifying machine learning model may be trained using an unsupervised machine learning algorithm and training data, comprising a plurality of inputs. Plurality of inputs may include any plurality of inputs described above, in reference to FIGS. 1-5. In some embodiments, classifying machine learning model may be trained using a supervised machine learning algorithm and training data, comprising a plurality of inputs. In some embodiments, method 600 may additionally selecting classifying machine learning model 128 from a plurality of classifying machine learning models, as a function of at least a feature 108; wherein, the classifying machine learning model 128 was trained using training data, comprising a plurality of inputs. Inputs may include any inputs described above, in reference to FIGS. 1-5. Alternatively or additionally, in some embodiments, method 600 may additionally select training data, comprising a plurality of inputs, from a plurality of training data, as a function of at least one feature 108; and train classifying machine-learning model 128 using the training data.

Still referring to FIG. 6, at step 620, computing device 104 interfaces conversationally with a user, wherein interfacing conversationally includes: generating text 136 as a function of an intervention class 132 and at least a preference input 112; and interfacing conversationally using the generated text. Text 136 may include any text 136 described above in reference to FIGS. 1-5. In some embodiments, step 620 may additionally include natural language processing. Natural language processing may include any natural language processing described above, in reference to FIGS. 1-5. In some embodiments, step 620 additionally includes receiving a submission; recognizing at least a word from the submission, wherein recognizing at least a word additionally includes: inputting the submission to a language processing model; and recognizing the at least a word as a function of the language processing model; and generating a response as a function of the at least a word. In some cases, step 620 further includes training a language processing model, wherein training the language processing model additionally includes: inputting training data to a natural language processing algorithm; and training the language processing model as a function of the natural language processing algorithm.

Still referring to FIG. 6, in some embodiments, method 600 may additionally include training, using a computing device 104, a probabilistic machine learning model 120, wherein training the probabilistic machine learning model 120 includes: inputting training data to a machine learning algorithm, wherein the training data comprises a plurality of features; and training the probabilistic machine learning model 120 as a function of the machine learning algorithm.

Still referring to FIG. 6, in some embodiments, method 600 may additionally include training, using a computing device 104, a classifying machine learning model 128, wherein training the probabilistic machine learning model 128 includes: inputting training data to a machine learning algorithm, wherein the training data comprises a plurality of features; and training the classifying machine learning model 128 as a function of the machine learning algorithm.

Still referring to FIG. 6, in some embodiments, method 600 may additionally include waiting for a timeframe to elapse; receiving at least a second feature 108 associated with a user's condition and at least a second preference input 112; generating a second probabilistic output 124, wherein generating the second probabilistic output 124 includes inputting the at least a second feature to a probabilistic machine learning model 120; and generating the second probabilistic output 124 as a function of the probabilistic machine learning model 120; and classifying a second intervention class 132, wherein classifying a second intervention class 132 includes: inputting the second probabilistic output 124 and the at least a second feature 108 to a classifying machine learning model 128; and classifying the second probabilistic output 124 and the at least a second feature 108 to a second intervention class 132 as a function of the classifying machine learning model 128. Timeframe may include any timeframe described above, in reference to FIGS. 1-5.

Still referring to FIG. 6, in some embodiments, method 600 may additionally include generating at least a metric by operating a machine learning model input with an intervention class 132; and step 620 additionally may include processing a submission from user for at least a datum associated with the at least a metric. Metric may include any metric described above, in reference to FIGS. 1-5. Machine learning model may include any machine learning model described above, in reference to FIGS. 1-5. Datum may include any datum described above, in reference to FIGS. 1-5.

Still referring to FIG. 6, in some embodiments, method 600 may additionally include: generating at least a metric, wherein generating the at least a metric additionally includes: inputting the intervention class to a machine learning model; and, generating the at least a metric as a function of the machine learning model. In some cases, step 620 may additionally include: receiving a submission from a user; recognizing, using the computing device, at least a datum from the submission, wherein recognizing the at least a datum additionally includes: inputting the submission to a language processing model; and, recognizing the at least a datum as a function of the language processing model; wherein the at least a datum is associated with the at least a metric.

Figure 7:
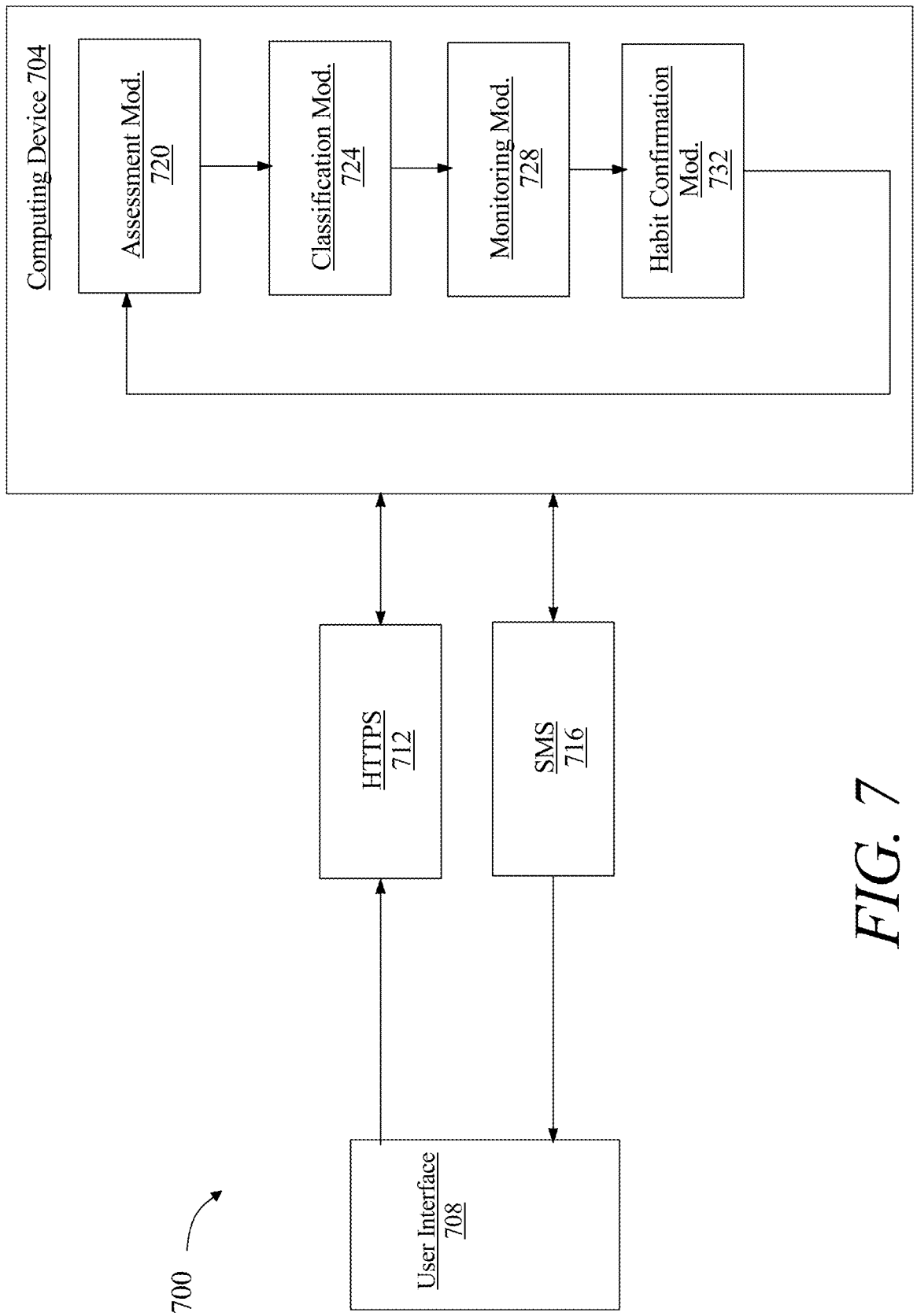
FIG. 7 is a block diagram illustrating an exemplary application according to some embodiments of the invention.

Referring now to FIG. 7, in some non-limiting embodiments, a system 700 is used for prophylactically treating and/or preventing a user's condition, such as without limitation Alzheimer's disease, other neurodegenerative disorders and/or other acute/chronic diseases, through one or more interventions. A computing device 704 may be communicative with a user device 708 by way of one or more networks. For example, in some cases communication over one or more networks may include communication by way of hypertext transfer protocol Secure (HTTPS) 712 and short message service (SMS) 716. In some cases, different communication protocols may be used for different functional purposes. As a non-limiting example, HTTPS 712 may be used for receiving information, i.e., at least a feature 108, relevant to a user's condition and/or performance of an assessment module 720 configured to assess a user's risk score, i.e., probabilistic output 124. Non-limiting examples of information 108 relevant to a user's condition may include one or more of responses to an interview (e.g., multiple choice selections), biometric data, genetic data, health information (e.g., at least a diagnosis), activity information (e.g., average number of steps per day), metrics indicating social connectivity (e.g., number of electronic human interactions per day), and cognitive test results or answers. In some embodiments, assessment module 720 may perform an assessment 720 using provided information 108 and any processes described above to generate a user's risk score 124. Next, a classification module 724 classifies a domain, i.e., an intervention class 132, in which to recommend an intervention. In some cases, a recommended intervention includes a lifestyle change within a domain 132, non-limiting exemplary domains 132 include diet, exercise, sleep, cognitive activity, and social engagement. Classification module 724 may function according to any method described throughout this application. Next, in some embodiments, a user may select a particular intervention related to a classified intervention class 132. For example, in some cases, an intervention class 132 relates to a user's behavior surrounding nutrition, or limiting sugar intake, and a user may be asked to select a single lifestyle change, i.e., preference input 112, from a list of possible lifestyle changes, including without limitation (1) limit dessert to once a week; (2) eat only fruit for dessert; and (3) eat only dark chocolate for dessert. Next, a monitoring module 728 may monitor a user's progress with an intervention, such as without limitation instituting and habitualizing a lifestyle or behavior change. In some embodiments, monitoring module 728 may interact with user device 708 by way of a test message 716. In some cases, text messages may be employed, because text-messages are intrusive and have an increased probability of response by a user. Monitoring module 728 may, for example, send a text message to a user device 708 asking "How many times in the past week did you eat dessert?" User may respond to this exemplary text message with a number. Positive progress, in this instance, may be indicated if a user had dessert no more than once in a past week. Ultimately, a habit confirmation module 732 may be implemented, for example after adequate progress has been made or a determined timeframe has elapsed. Habit confirmation 732 module may, in some embodiments, verify user has habitualized a lifestyle change or other intervention. In some cases, habit confirmation module 732 may additionally recollect information 108 related to a user's condition; as in some cases, assessment module 720 performs a re-assessment and treatment process iteratively progresses again.

Still referring to FIG. 7, in some embodiments a second user device may be in communication with computing device 704. In some cases, a second user familiar with user, such as without limitation a friend or family member, may be involved in intervention. For example, in some cases, a second user may be informed of a user's current intervention or lifestyle change; the second user may be supportive of the user's compliance with the intervention.

Still referring to FIG. 7, in some embodiments before a user is asked to engage with a communication with a computing device 704, the user may be asked if ready? Only after communicating that user is ready may computing device 704 engage with a communication with user, for example by taking a cognitive assessment.

Still referring to FIG. 7, in some embodiments communication between user and computing device 704 may include educational materials for a user. In some cases, educational materials may be related to an intervention or intervention class 132 that is presently being considered by user. Educational materials may attempt to educate a user as to why a particular intervention is worthwhile; how a particular intervention will work; or how a user may be able to be successful with a particular intervention.

Figure 8:
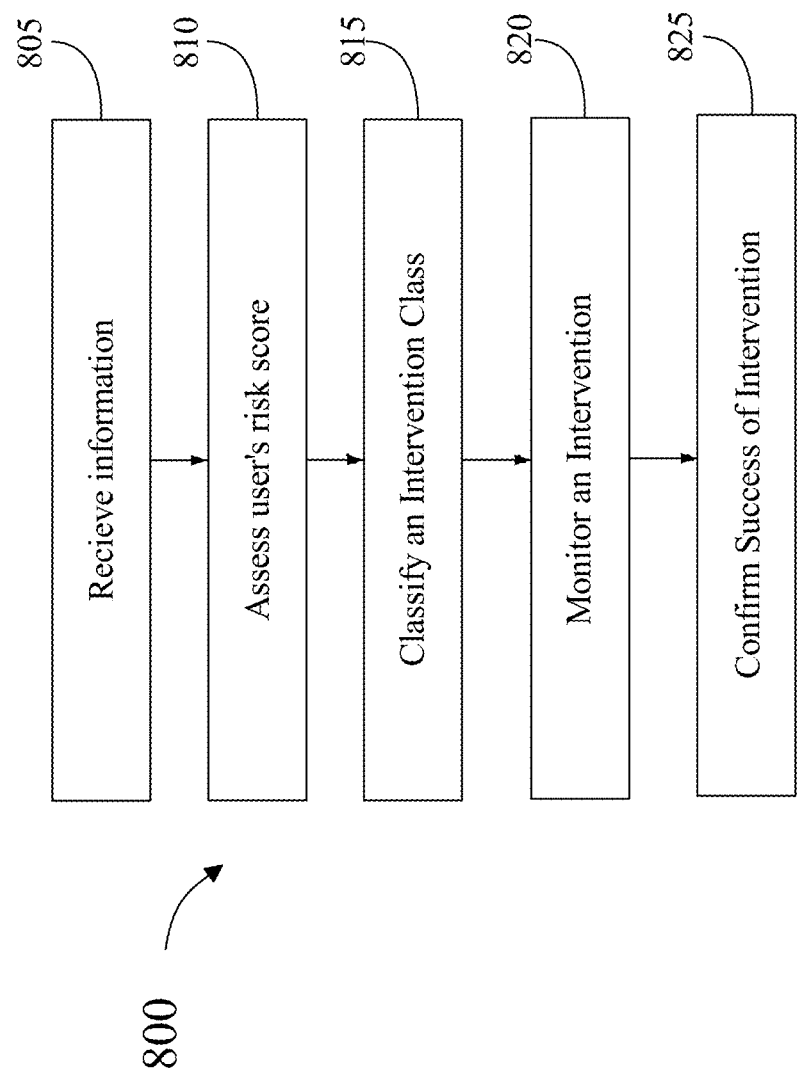
FIG. 8 is a flow diagram illustrating an exemplary application according to some embodiments of the invention.

Referring now to FIG. 8, some non-limiting embodiments may relate to a method 800 of prophylactically treating a user's condition through one or more interventions, such as without limitation Alzheimer's disease. At step 805, a computing device 704 may receive information relevant a user's condition. Non-limiting examples of information 108 relevant to a user's condition may include one or more of responses to an interview (e.g., multiple choice selections), biometric data, genetic data, health information (e.g., at least a diagnosis), activity information (e.g., average number of steps per day), metrics indicating social connectivity (e.g., number of electronic human interactions per day), and cognitive test results or answers. At step 810, computing system 704 may assess a user's risk score, i.e., probabilistic output 124. Step 810 may include performing one or more of any processes described in this disclosure. At step 815, computing device 704 may classify an intervention class 132. Step 815 may include performing one or more of any processes described in this disclosure. At step 820, computing device 704 may monitor an intervention. In some embodiments, step 820 may include conversationally interfacing with a user, such as without limitation by way of SMS. Step 820 may include performing one or more of any processes described in this disclosure. At step 825, computing device may confirm success of an intervention. In some embodiments, step 825 may include waiting for a timeframe to elapse and/or one or more user inquiries. Step 825 may include one or more of any processes described in this disclosure.

Although present disclosure has been described in detailed above, it will be understood by those of ordinary skill in the art that the additional embodiments and applications are envisioned by the present disclosure. For example, in some additional embodiments, a user's risk score may be assessed based upon a series of question-and-answer routines. In some cases, categories and/or subcategories of lifestyle choices, and the like, may be defined for example by an expert user such as without limitation a clinician. In some cases, a clinician may assign risk value to one or more classifications including, without limitation nutrition, exercise, sleep hygiene, and the like. In some cases, an expert may define categories and assign risks to them. In some cases, an expert may develop a patient question and answer routine. In some cases, question and answer routine may be developed in order to facilitate communication of information associated with patient risks. Clinicians can assign a risk value to individual questions and responses. In some cases, a hierarchy of questions, responses, and the like, is built according to their respective risk weight.

In some cases, a question-and-answer routine may be used to assess user risk, set priorities for user behavioral changes, make targeted instruction for lifestyle changes, and/or guide a user through text communication with lifestyle changes. For example, responses that correspond to a high-risk category may then lead system to prioritize that category for intervention. Question-and-answer routine may be repeated cyclically and/or periodically to determine and continually update risk scores, reset priorities, and the like. In some cases, risk-based hierarchies of categories, features and the like may contribute to increased scalability and ease of use.

In a non-limiting exemplary use case, topics may have relative weights as well as categories, so while exercise for instance may have more weight than "brain training," extremely high-risk responses within the lower weight category could still cause that one to be prioritized. For example without limitation, patient does exercise, and all exercise question-and-answer responses are low-risk, while user responses are all high-risk in terms of cognitive activity (e.g., "I don't read, I don't challenge my brain, I don't do puzzles," and the like) may cause interventions that prioritize cognitive to be suggested.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
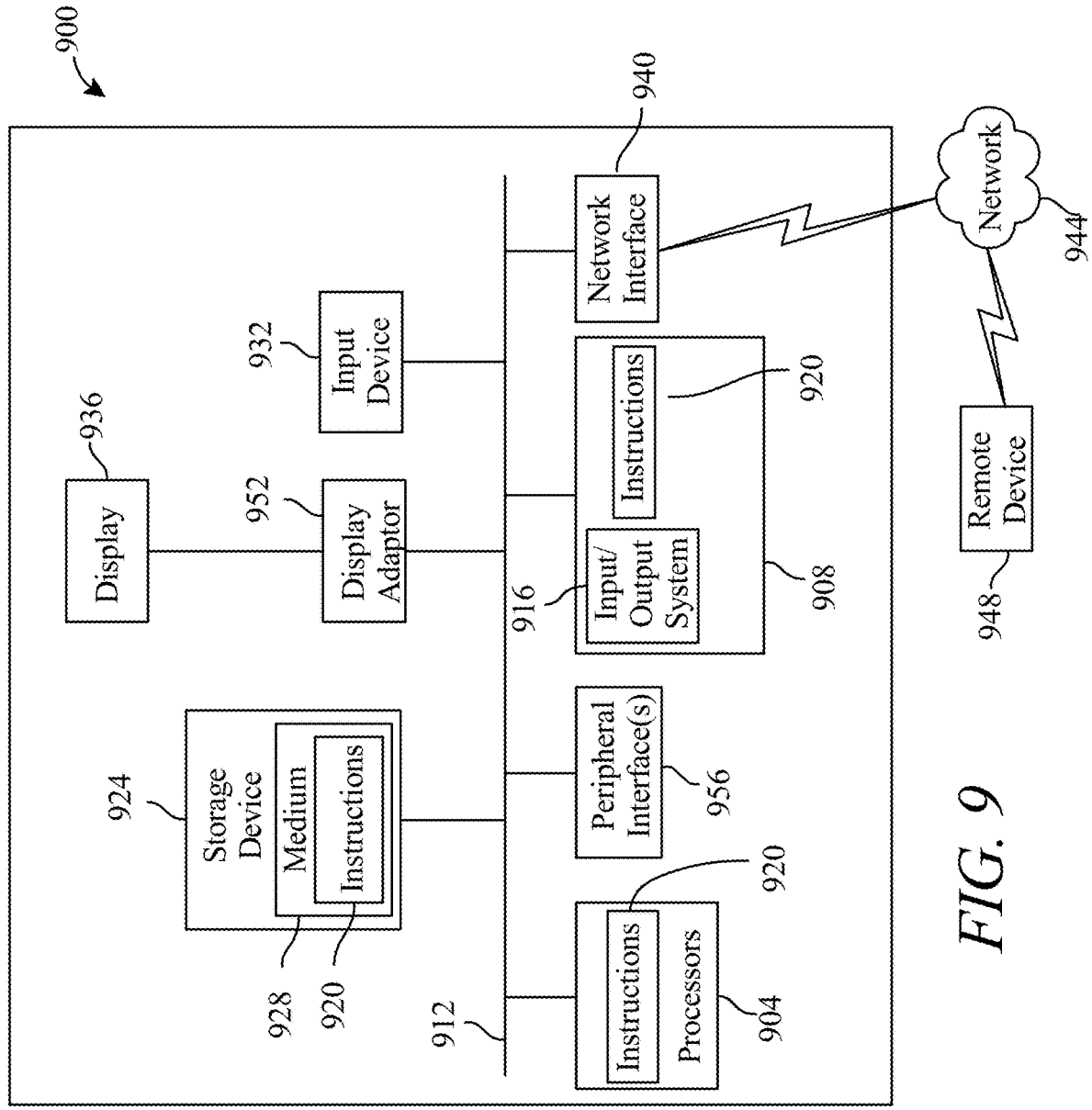
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown. Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of text-based conversation with a user, using machine learning, the method comprising:
receiving, using a computing device, at least a feature associated with a user's condition and at least a preference input;
generating, using the computing device, a probabilistic output, wherein generating the probabilistic output further comprises:
inputting the at least a feature to a probabilistic machine learning model; and,
generating the probabilistic output as a function of the probabilistic machine learning model;
classifying, using the computing device, the probabilistic output and the at least a feature to an intervention class, wherein classifying further comprises:
inputting the probabilistic output and the at least a feature to a classifying machine learning model; and
classifying the probabilistic output and the at least a feature to the intervention class as a function of the classifying machine learning model;
interfacing conversationally, using the computing device, with the user, wherein interfacing conversationally further comprises:
generating text as a function of the intervention class and the at least a preference input; and
interfacing conversationally using the generated text;
waiting, using the computing device, for a timeframe to elapse;
receiving, using the computing device, at least a second feature associated with the user's condition and at least a second preference input;
generating, using the computing device, a second probabilistic output, wherein generating the second probabilistic output further comprises:
inputting the at least a second feature to the probabilistic machine learning model; and
generating the second probabilistic output as a function of the probabilistic machine learning model; and
classifying, using the computing device, a second intervention class, wherein classifying the second intervention class further comprises:
inputting the second probabilistic output and the at least a second feature to the classifying machine learning model; and
classifying the second probabilistic output and the at least a second feature to the second intervention class as a function of the classifying machine learning model.

2. The method of claim 1, further comprising:
training, using the computing device, the probabilistic machine learning model, wherein training the probabilistic machine learning model further comprises:
inputting training data to a machine learning algorithm, wherein the training data comprises a plurality of features correlated to a probabilistic outcome; and
training the probabilistic machine learning model as a function of the machine learning algorithm.

3. The method of claim 1, further comprising:
training, using the computing device, the classifying machine learning model, wherein training the classifying machine learning model further comprises:
inputting training data to a machine learning algorithm, wherein the training data comprises a plurality of features; and
training the probabilistic machine learning model as a function of the machine learning algorithm.

4. The method of claim 1, wherein interfacing conversationally further comprises:
receiving, using the computing device, a submission;
recognizing, using the computing device, at least a word from the submission, wherein recognizing the at least a word further comprises:

inputting the submission to a language processing model; and
recognizing the at least a word as a function of the language processing model; and
generating, using the computing device, a response as a function of the at least a word.

5. The method of claim 4, further comprising:
training, using the computing device, the language processing model, wherein training the language processing model further comprises:
inputting training data to a natural language processing algorithm; and
training the language processing model as a function of the natural language processing algorithm and the training data.

6. The method of claim 1, further comprising:
generating, using the computing device, at least a metric, wherein generating the at least a metric further comprises:
inputting the intervention class to a machine learning model; and
generating the at least a metric as a function of the machine learning model.

7. The method of claim 6, wherein interfacing conversationally further comprises:
receiving, using the computing device, a submission from the user;
recognizing, using the computing device, at least a datum from the submission, wherein recognizing the at least a datum further comprises:
inputting the submission to a language processing model; and
recognizing the at least a datum as a function of the language processing model;
wherein the at least a datum is associated with the at least a metric.

8. The method of claim 1, further comprising selecting the classifying machine learning model from a plurality of classifying machine learning models as a function of the at least a feature.

9. The method of claim 1, further comprising selecting training data as a function of the at least a feature; and
training the classifying machine-learning model using the training data.

10. A system for text-based conversation with a user, using machine learning, the system comprising a computing device configured to:
receive at least a feature associated with a user's condition and at least a preference input;
generate a probabilistic output, wherein generating the probabilistic output further comprises:
inputting the at least a feature to a probabilistic machine learning model; and,
generating the probabilistic output as a function of the probabilistic machine learning model;
classify the probabilistic output and the at least a feature to an intervention class, wherein classifying further comprises:
inputting the probabilistic output and the at least a feature to a classifying machine learning model; and
classifying the probabilistic output and the at least a feature to the intervention class as a function of the classifying machine learning model;
interface conversationally with the user, wherein interfacing conversationally further comprises:
generating text as a function of the intervention class and the at least a preference input; and
interfacing conversationally using the generated text;
wait for a timeframe to elapse;
receive at least a second feature associated with the user's condition and at least a second preference input;
generate a second probabilistic output, wherein generating the second probabilistic output further comprises:
inputting the at least a second feature to the probabilistic machine learning model; and
generating the second probabilistic output as a function of the probabilistic machine learning model; and
classify a second intervention class, wherein classifying the second intervention class further comprises:
inputting the second probabilistic output and the at least a second preference input to the classifying machine learning model; and
classifying the second probabilistic output and the at least a second preference input to the second intervention class as a function of the classifying machine learning model.

11. The system of claim 10, wherein the computing device is further configured to:
train the probabilistic machine learning model, wherein training the probabilistic machine learning model further comprises:
inputting training data to a machine learning algorithm, wherein the training data comprises a plurality of features correlated to a probabilistic outcome; and
training the probabilistic machine learning model as a function of the machine learning algorithm.

12. The system of claim 10, wherein the computing device is further configured to:
train the classifying machine learning model, wherein training the classifying machine learning model further comprises:
inputting training data to a machine learning algorithm, wherein the training data comprises a plurality of features; and
training the machine learning model as a function of the machine learning algorithm.

13. The system of claim 10, wherein interfacing conversationally further comprises:
receiving, using the computing device, a submission;
recognizing, at least a word from the submission, wherein recognizing the at least a word further comprises:
inputting the submission to a language processing model; and
recognizing the at least a word as a function of the language processing model; and
generating a response as a function of the at least a word.

14. The system of claim 13, wherein the computing device is further configured to:
train the language processing model, wherein training the language processing model further comprises:
inputting training data to a natural language processing algorithm; and
training the language processing model as a function of the natural language processing algorithm and the training data.

15. The system of claim 10, wherein the computing device is further configured to:
generate at least a metric, wherein generating the at least a metric further comprises:
input the intervention class to a machine learning model; and
generate the at least a metric as a function of the machine learning model.

16. The system of claim 15, wherein the computing device is further configured to:
   receive a submission from the user;
   recognize at least a datum from the submission, wherein recognizing the at least a datum further comprises:
      inputting the submission to a language processing model; and
      recognizing the at least a datum as a function of the language processing model;
   wherein the at least a datum is associated with the at least a metric.

17. The system of claim 10, wherein the computing device is further configured to select the classifying machine learning model from a plurality of classifying machine learning models, as a function of the at least a feature, wherein the classifying machine learning model was trained using training data.

18. The system of claim 10, wherein the computing device is further configured to:
   select training data from a plurality of training data, as a function of the at least a feature; and
   train the classifying machine learning model using the training data.

\* \* \* \* \*